(12) United States Patent
Tenerz et al.

(10) Patent No.: US 8,579,825 B2
(45) Date of Patent: Nov. 12, 2013

(54) ELECTRICALLY CONDUCTIVE GUIDE WIRE

(75) Inventors: Lars Tenerz, Uppsala (SE); Pär von Malmborg, Uppsala (SE)

(73) Assignee: Radi Medical Systems AB, Uppsala (SE)

( * ) Notice: Subject to any disclaimer, the term of this patent is extended or adjusted under 35 U.S.C. 154(b) by 1702 days.

(21) Appl. No.: 10/390,185

(22) Filed: Mar. 18, 2003

(65) Prior Publication Data

US 2003/0220588 A1    Nov. 27, 2003

Related U.S. Application Data

(63) Continuation-in-part of application No. 10/170,415, filed on Jun. 14, 2002, now Pat. No. 7,011,636.

(60) Provisional application No. 60/299,233, filed on Jun. 18, 2001.

(30) Foreign Application Priority Data

Jun. 15, 2001    (EP) ..................................... 01850107

(51) Int. Cl.
*A61B 5/00* (2006.01)
*A61B 5/02* (2006.01)

(52) U.S. Cl.
USPC ......................................... 600/488; 600/585

(58) Field of Classification Search
USPC .......................... 600/585, 467, 407, 462, 463
See application file for complete search history.

(56) References Cited

U.S. PATENT DOCUMENTS

| | | | |
|---|---|---|---|
| 5,174,295 A | 12/1992 | Christian et al. | |
| 5,226,423 A | 7/1993 | Tenerz et al. | |
| 5,240,437 A | 8/1993 | Christian | |
| 5,517,989 A | 5/1996 | Frisbie et al. | |
| 5,697,380 A | 12/1997 | Quiachon et al. | |
| 5,749,357 A * | 5/1998 | Linder ...................... 128/200.26 |
| 6,039,699 A | 3/2000 | Viera | |
| 6,106,476 A * | 8/2000 | Corl et al. ...................... 600/486 |
| 6,106,486 A | 8/2000 | Tenerz et al. | |
| 6,112,598 A | 9/2000 | Tenerz et al. | |
| 6,142,958 A | 11/2000 | Hammarström et al. | |
| 6,159,141 A * | 12/2000 | Apple et al. ...................... 600/3 |
| 6,224,585 B1 * | 5/2001 | Pfeiffer ........................ 604/523 |

(Continued)

FOREIGN PATENT DOCUMENTS

| EP | 0 673 621 A1 | 9/1995 |
|---|---|---|
| EP | 0 925 803 A2 | 6/1999 |

*Primary Examiner* — Brian Szmal
*Assistant Examiner* — Fangemonique Smith
(74) *Attorney, Agent, or Firm* — Foley & Lardner LLP (57) ABSTRACT

The present invention relates to a measuring device, insertable into a living body. The device includes an elongated flexible member in the form of a thick-walled hollow tube with a proximal end and a distal end. The tube defines a central lumen with an inner wall. The lumen may contain a core and an insulating material provided between the core and the inner wall. The core may be made of an electrically conductive material and may be of essentially constant diameter over its entire length. Alternatively, the lumen may contain at least two electrical leads. An electrical sensor is attached to the distal end of the elongated flexible member and is electrically connected to the core.

39 Claims, 8 Drawing Sheets

(56) References Cited

U.S. PATENT DOCUMENTS

| | | | |
|---|---|---|---|
| 6,547,788 B1 * | 4/2003 | Maguire et al. | 606/41 |
| 6,607,502 B1 * | 8/2003 | Maguire et al. | 604/22 |
| 6,615,071 B1 * | 9/2003 | Casscells et al. | 600/474 |
| 6,796,945 B2 * | 9/2004 | Belef et al. | 600/467 |
| 2001/0037066 A1 * | 11/2001 | Smith | 600/462 |

* cited by examiner

ELECTRICALLY CONDUCTIVE GUIDE WIRE

This application is a continuation-in-part of U.S. application Ser. No. 10/170,415 filed Jun. 14, 2002, which is the non-provisional application of U.S. Provisional Patent Application No. 60/299,233 filed Jun. 18, 2001. The applicants also claim priority to European Application No. 01850107.2 filed Jun. 15, 2001. The entire contents of all three of these applications are incorporated herein by reference.

BACKGROUND

1. Field of the Invention

The present invention relates generally to guide wire/sensor assemblies, wherein there are at least two electrical leads or conductors required for energizing the sensor and for signal transmission, said leads extending along the length of the guide wire between a proximal end and a distal end. In particular it relates to a coaxial, electrically conductive guide wire provided with an electrical sensor.

2. Description of the Related Art

For medical purposes many devices and applications have been disclosed and patented, wherein a miniaturized sensor is positioned in the distal region of a guide wire or a catheter. Such sensors can have various purposes, such as the measurement of pressure, temperature, flow, or for the detection of some property in vivo in a living body, e.g., pH, $O_2$, $CO_2$, etc.

For most applications it is required that the sensors be energized electrically, and the response be transmitted back to the exterior of the patient via electrical signals. Some applications use optical sensor devices having fiber optic signal transmission, but these fall outside the scope of the present invention.

Thus, some means of signal and energy transmission is required, and most commonly extremely thin electrical leads are provided inside the guide wire, which itself is provided in the form of a tube (of the order of 0.35 mm in outer diameter), oftentimes made of steel. In order to increase the bending strength of the tubular guide wire, a core wire is positioned inside the tube. The mentioned electrical leads are positioned in the space between the inner lumen wall and the core wire.

This design has certain drawbacks. First, it renders the assembly non-rotationally symmetric, since it is virtually impossible to distribute the electrical leads uniformly over the circumference of the core wire inside the space between the inner lumen wall and the core wire. An asymmetric configuration of leads gives rise to different bending properties in different directions of bending.

Second, there is a risk that the extremely thin leads (although coated with an insulating layer) will become damaged due to friction forces appearing in the lumen, in particular at junctions in the proximal and distal regions, where the core wire changes dimension, and where manipulations during manufacture (e.g. soldering) can cause damage to the coating and possibly cause a short-circuit.

Third, it is relatively complicated to assemble the device because of the extremely small dimensions of tubes, leads and sensors. And, fourth, electrical contacts at the proximal end of the guide wire are made using discrete components, thereby complicating the assembly.

A guide wire disclosed in EP 0 925 803, assigned to the same assignee as the present invention, attempts to solve the symmetry problem by providing electrical leads in the form of concentric layers of conducting material with insulation provide between layers. Although representing an improvement, this device also has certain drawbacks. For example, there is a risk that the concentric layers may break and cause a short-circuit. Another possible problem could be "pinholes" in the very thin insulating layers, representing a potential risk for short-circuiting.

SUMMARY

Thus, in view of the problems with the prior art devices, it is the object of the present invention to provide a guide wire design that overcomes the drawbacks of the prior art sensor/guide wire assembly designs.

Therefore, a measuring device, insertable into a living body, is provided which comprises an elongated flexible member having a proximal end and a distal end and a central lumen with an inner wall, a core filling said lumen, an insulating material provided between said core and said inner wall, said core being made of an electrically conductive material and having an essentially constant diameter over its entire length, an electrical sensor attached to the distal end of said elongated flexible member, said electrical sensor being electrically coupled to said core.

By making the guide wire from a coaxial wire, in particular having a central core of essentially constant diameter, the cost of manufacturing is lowered and the complexity by which the guide wire is manufactured is reduced.

The manufacturing process can be implemented as a continuous process, wherein long lengths of wire can be made, as opposed to the prior art device, where the wire must be made piece by piece.

Also, the guide wire becomes rotationally symmetric, which is a significant advantage in terms of ease of manipulation of the device by a physician when using the device.

Furthermore, the structure is much less prone to develop "pin holes" that could lead to short circuiting problems.

BRIEF DESCRIPTION OF THE DRAWINGS

The invention will now be described in greater detail with reference to the attached drawings, in which.

DETAILED DESCRIPTION

Figure 1:
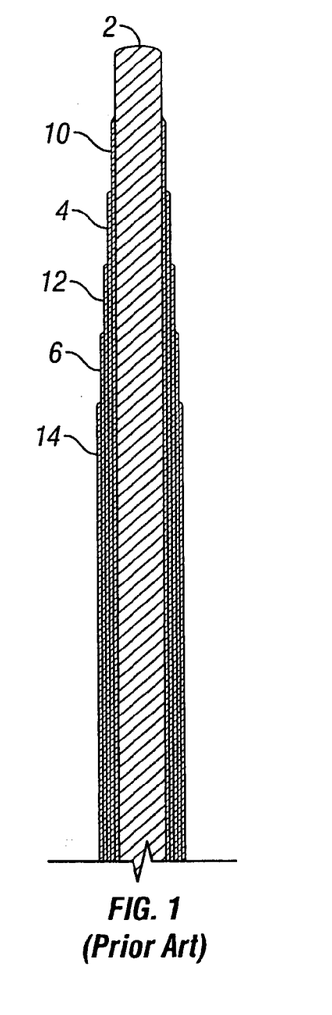
FIG. 1 is a longitudinal cross-sectional view through a prior art guide wire according to EP 0 925 803.

FIG. 1 illustrates a prior art guide wire according to EP 0 925 803 in cross section in the longitudinal direction. It comprises a core wire 2, on which a plurality of concentric layers 4, 6 of conductive material have been provided. Between the conductive layers there are insulating layers 10, 12, and another insulating layer 14 is provided on top of layer 6. In addition to the drawbacks mentioned in the discussion of the background of the invention, the manufacturing process is rather complex, either by a complex extrusion process or by a process involving a consecutive deposition of the various layers.

Figure 2:
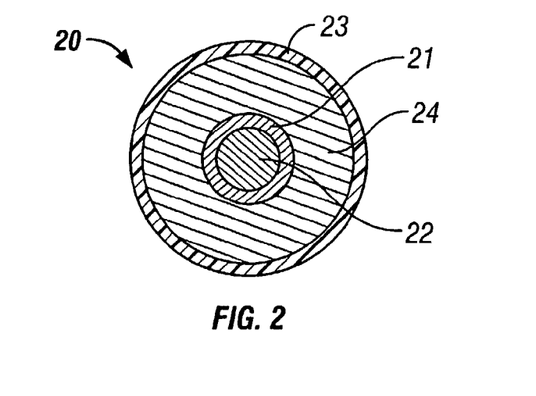
FIG. 2 is a cross-sectional view through a first embodiment of a coaxial guide wire suitable for use in the invention.

FIG. 2 illustrates the key feature of the present invention. It shows a cross section through a guide wire 20 having a central core 22 of a conductive material (e.g. stainless steel or superelastic metal (e.g. Nitinol®)) disposed within the lumen of a thick-walled tube 24 also of a conductive material (e.g. stainless steel or superelastic metal (e.g. Nitinol®)). There is an insulating layer 21 between the core 22 and the tube 24.

This structure of the core/insulator/tube can suitably be manufactured by an extrusion process, or by shrinking a tube onto a core. Thus, the core is located inside the tube in a tight fit. The outer surface of the tube 24 is preferably covered by an insulating layer 23, in order to protect the wire from blood and other fluids, which could otherwise cause short circuiting. The insulating material usable with the invention for the outer surface layer 23, can e.g. be selected among a number of polymer materials, Teflon®, poly-imide or Parylene™, just to mention a few. Also ceramic type materials, e.g. alumina or silicon nitride, in its various possible forms can be used. For the intermediate layer 21, however, the ceramic materials may not be suitable, and therefor polymer materials of the same type as mentioned above are used.

The diameter of the core over its entire length is constant, and is suitably less than 50% of the outer diameter of the elongated flexible member (and is preferably less than 25% thereof), except in the distal end, where the outer layer is reduced in order to provide the necessary constructive details, as later described.

The constant diameter of the core is a significant advantage over the prior art structure according to EP 0 925 803, in that it makes possible a continuous manufacturing process whereas the '803 structure must be made piece by piece. Thus, by using a coaxial wire according to the teachings herein, the manufacturing time will be considerably reduced and simplified, and therefore, much more economical.

Other great benefits of this structure include: (a) that it is rotationally symmetric; (b) that the torque can be controlled by controlling the relative dimensions of core and tube; and (c) that the mounting of a sensor element on the guide wire becomes very simple, as will later be described in further detail.

Figure 3:
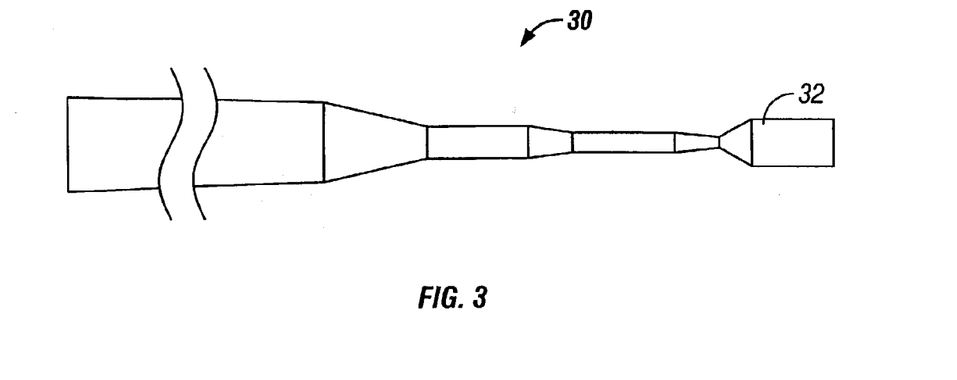
FIG. 3 is a schematic cross-section in the longitudinal direction of a guide wire suitable for use according to the invention.

FIG. 3 is a schematic view of an embodiment of an elongated flexible member forming a guide wire, generally designated with reference numeral 30, having the basic construction of FIG. 2, however shown without certain details at the distal end (protective coil, sensor etc). The various segments of the wire are not shown to scale, and the total length of the wire is typically about 1.80 meters, although other lengths are possible, even up to about 3 meters.

As can be seen in FIG. 3 the diameter of the elongated flexible member varies, and in the distal end has segments of reduced diameter to increase the flexibility of the wire in the distal region. However, the very distal end portion 32, which comprises a thicker portion forming a mounting structure for the sensor, has a thickness corresponding to the diameter of the wire in its proximal region (e.g. approximately 0.35 mm).

This thicker portion 32 comprises a mount (shown in FIGS. 4a and 4b) for a sensor element. This mounting structure comprises a recess, having a bottom surface in a first portion of which the core is exposed so as to form a first contact surface for the sensor (i.e., the mounting structure forms an arrangement which is in accordance with the teachings of our U.S. Pat. No. 6,142,958 (incorporated herein by reference)).

Figure 4A:
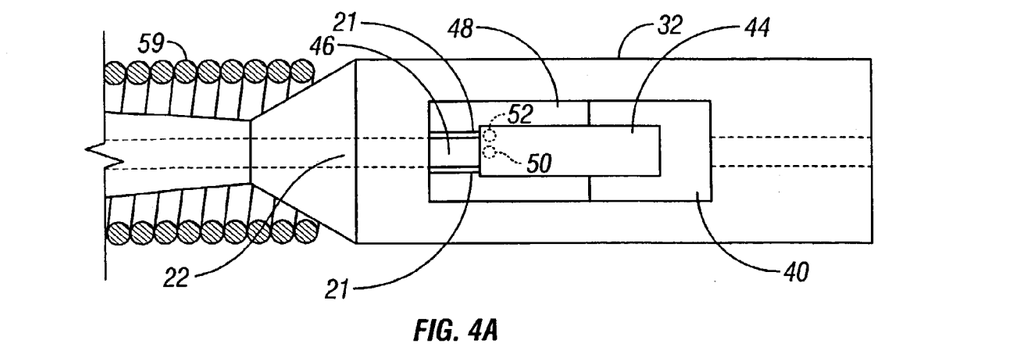
FIG. 4A shows, in greater detail, the distal end portion with a sensor mount, and a sensor mounted therein, in a top view.
Figure 4B:
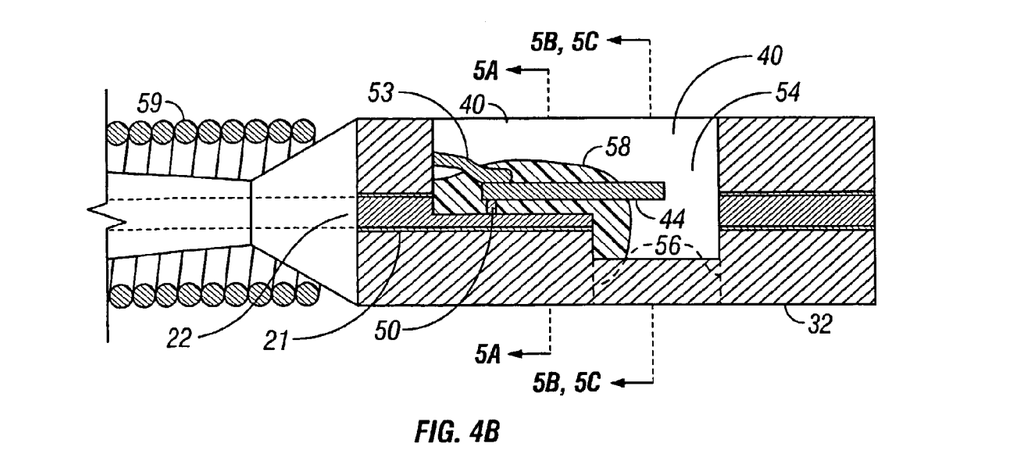
FIG. 4B shows a cross sectional view in longitudinal direction of the device shown in FIG. 4A.
Figure 5A:
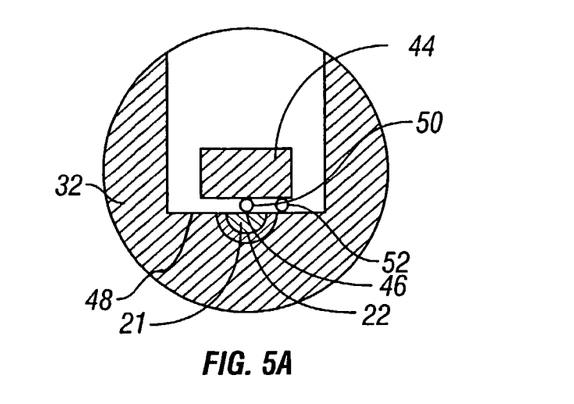
FIG. 5A shows a cross sectional view taken along line 5A-5A in FIG. 4B.
Figure 5B:
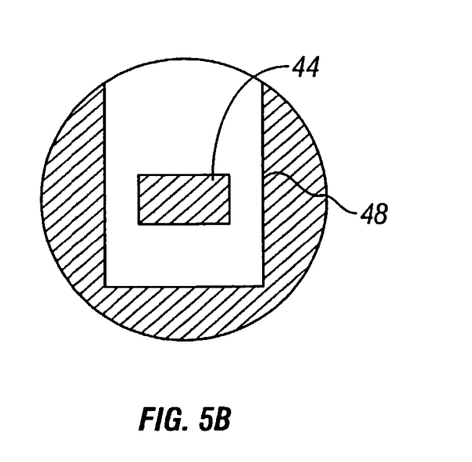
FIG. 5B shows a cross sectional view taken along line 5B-5B in FIG. 4B.
Figure 5C:
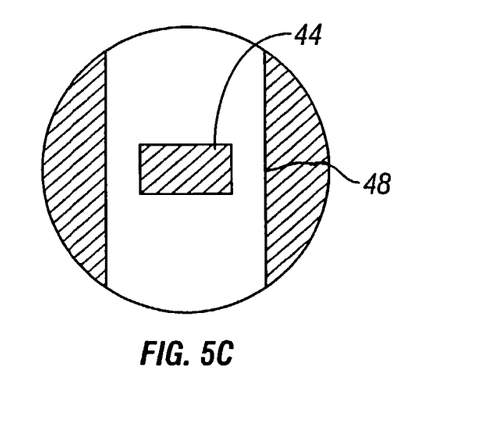
FIG. 5C shows a cross sectional view taken along line 5C-5C in FIG. 4B.

FIGS. 4A and 4B illustrate the distal end portion 32 of one embodiment in greater detail. FIG. 4A shows the sensor mount in a top view and FIG. 4B shows a side view with parts in cross section. FIGS. 5A-5C are cross sections taken along lines 5A-5A, 5B-5B, and 5C-5C, respectively.

Thus, the thicker distal sensor mount portion 32 has a recess 40 formed therein (which is formed by suitable machining, e.g., EDM cutting or laser cutting) which constitutes said sensor mount for a miniaturized sensor 44. Thereby, the bottom surface of the recess will exhibit two regions of conductive material. Namely, the central core 22 (indicated with broken lines in the part not shown in cross section) will be exposed to form a first contact surface 46, separated from the bulk material of the tube by the insulation material 21. The bulk material of the tube will form a second contact surface 48.

A sensor chip 44 having two contact terminals 50, 52 (located on the bottom side of the sensor chip, indicated by circles in broken lines), can thus be attached by suitable bonding or soldering to these surfaces, as can be seen in FIG. 4B. In this way, electrical energy can be supplied for energizing purposes in the two leads formed by the core and the tube, respectively. By suitable techniques for modulation of the energizing current, the same leads can be used for signal transmission.

In the shown embodiment, the recess 40 has a deeper portion 54 in the region where the sensitive part of the sensor chip 44 is positioned, such that the sensitive part of the chip extends out over the deeper recess part 54, which is seen in FIG. 4B. This is in accordance with the teachings in our U.S. Pat. No. 6,112,598 (incorporated herein by reference), and reduces or even eliminates bending artifacts.

The recess in this embodiment reaches through the core 22.

In an alternative design, the deeper recess portion can extend all the way through the thicker portion, as indicated by broken lines 56 in FIG. 4B. Such a design would yield a cross section of the type shown in FIG. 5C which is taken along line 5C-5C in FIG. 4B.

In this embodiment the diameter of the enlarged sensor mount portion 32 has the same diameter as the diameter of the guide wire. Therefore, it is not possible to attach the coil 59 by sliding it over the wire. Instead it must be wound onto the wire at the correct position, i.e., proximally of the sensor mount.

FIG. 5A shows a cross section taken along line 5A-5A in FIG. 4B. Here it can be clearly seen how the sensor chip 44 is attached to the two contact surfaces 46 and 48, respectively, by the contact terminals 50, 52 respectively.

An alternative way of connecting the sensor chip to the outer tube is by bonding an electrical lead 53 thereto. Thereby eliminating the contact terminal 52.

FIG. 5B shows the cross section taken along line 5B-5B in FIG. 4B, which clearly illustrates the "cantilevering" end of the sensor chip.

In order not to short circuit the core 22 and the outer tube material 32, when the recess is exposed to body fluids, the inner surface of the recess must be covered with some protective material 58 (not shown in FIGS. 5A-5C). This can be easily achieved by providing silicone or some similar material to cover at least those areas where fluids could cause a short circuit.

Figure 6A:
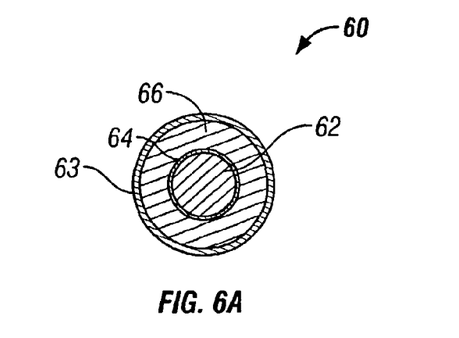
FIG. 6A shows a cross sectional view of a second embodiment of a coaxial guide wire suitable for use in the invention.

In the embodiment described above with reference to FIGS. 4-5, the core has a relatively small diameter compared to the surrounding tube. However, it is also possible to make a coaxial guide wire 60 with a thicker core 62, and a thick-walled outer tube 66 with an insulating layer 64 provided between the core and the tube, as shown in FIG. 6A. In addition, preferably an insulating layer 63 is applied to the outer surface of the tube 66. In this embodiment, the diameter of the core 62 is greater than the thickness of the outer tube 66.

Figure 6B:
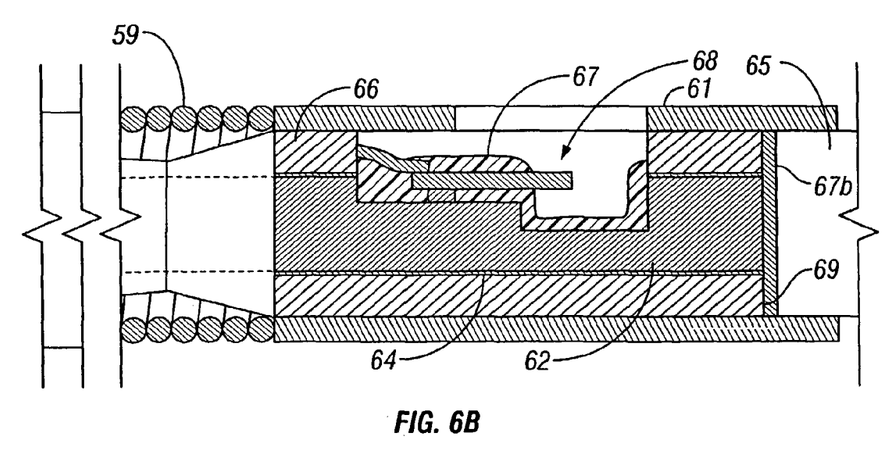
FIG. 6B is a longitudinal cross sectional view through a sensor and guide wire assembly according to a second embodiment, namely the distal end portion with a sensor mount, and a sensor mounted therein.

In this embodiment, the recess 68 forming the sensor mount will not reach all the way through the core 62, as can be seen in FIG. 6B. This requires that the entire bottom surface and parts of the walls of the recess 68 be covered with insulating material 67. It also necessitates protection of the distal end surface 69 of the core with insulating material 67b so that the very distal tip 65 that is to be attached thereto will not be in electrical contact with the inner core 62. For the purpose of securing the tip 65, it is convenient to provide a piece of tubing 61 over the enlarged portion forming the sensor mount.

This piece of tubing extends slightly beyond the distal end 69, so as to form a cylindrical recess in which the proximal end of the tip 65 can be inserted, and secured by soldering, gluing, or shrinking. Thus, in this case the sensor mount has a diameter that is smaller than the diameter of the wire 60. Therefore, in this case the coil 59 can be slid over the mount and secured by soldering or gluing, before the piece of tubing 61 is positioned on the mount.

In a further advantageous aspect of the invention, the novel guide wire design provides for a very simple way to construct a proximal male connector, for connecting the guide wire assembly to external equipment.

Figure 7A:
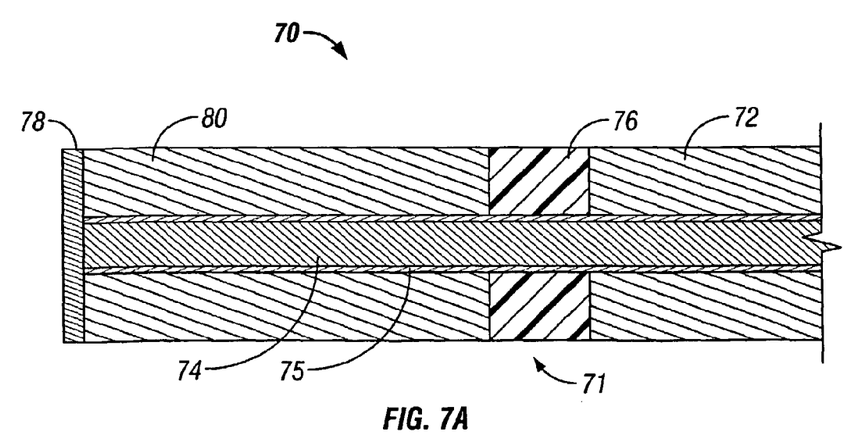
FIG. 7A shows a proximal contact.

In FIG. 7A the proximal end 70 of a guide wire 80 is shown in cross section. It comprises an outer tube member 72, an inner core 74 with an insulating layer 75 disposed between said core and said tube.

Figure 7B:
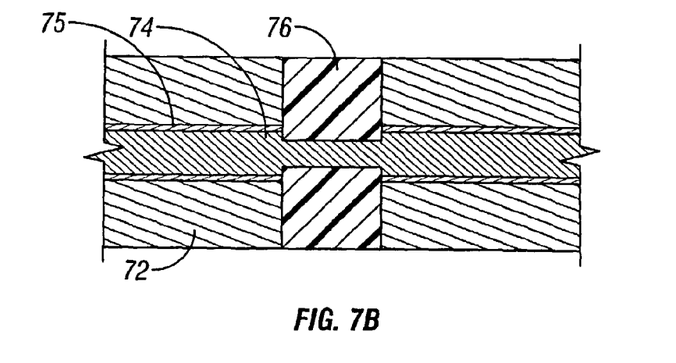
FIG. 7B shows a second embodiment of a proximal contact.

In order to make a connector having two contact elements or surfaces, a circumferential recess 71 is made in the outer tube 72, down to the insulating layer 75 (this embodiment is shown in FIG. 7A), or through the insulating layer 75 down to a depth at which the inner core 74 is exposed (FIG. 7B). It is of course essential that there be no electrical connection between the distal and the proximal end of the outer tube. The recess is filled with an insulating material 76, e.g. some polymer (Teflon®, poly-imide or Parylene or the like) or an inorganic material such as ceramic type materials, e.g. alumina or silicon nitride, in its various possible forms.

Finally, the very end surface of the coaxial wire 80 is "capped" with a layer 78 of conductive material so as to short circuit the core 74 with the proximal end portion of the tube, now electrically insulated from the remainder of the tube on the distal side of the recess 71 filled with insulating material 76.

Figure 8:
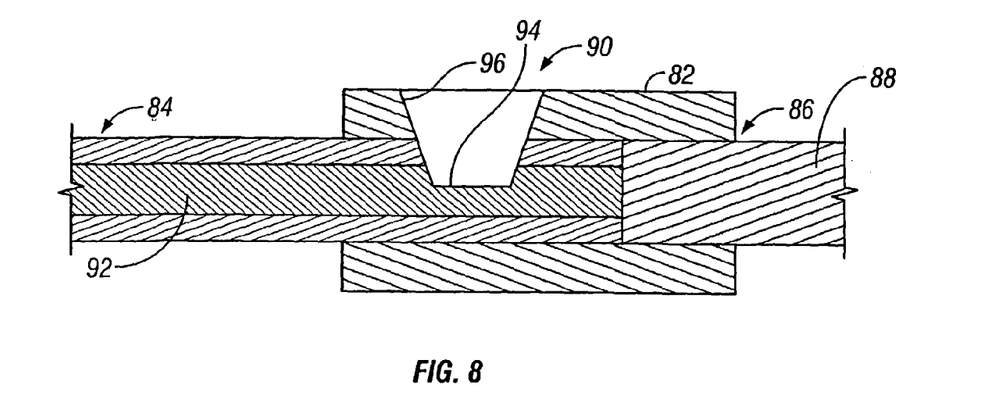
FIG. 8 illustrates a further embodiment of a sensor and guide wire assembly according to the invention.

FIG. 8 illustrates an alternative way of providing the sensor mount at the distal end of the wire.

It encompasses providing a tube segment 82 having an inner diameter corresponding to the outer diameter of the coaxial wire 84, and positioning said tube segment 82 over the distal end of the wire 84. Thereby a portion of the tube segment 82 should extend around the wire 84 so as to form a cylindrical recess 86 at the distal end. This recess will be used for attaching a tip 88 by press fitting and/or soldering.

When the tube 82 is mounted on the wire 84, a recess 90 is formed by any suitable technique, e.g., EDM cutting or laser cutting, down to a depth such that the inner core 92 is exposed. The exposed bottom surface 94 can be used as a first contact surface for a sensor element (not shown). The walls 96 of the recess 90 can be used as a second contact surface for said sensor.

Figure 9:
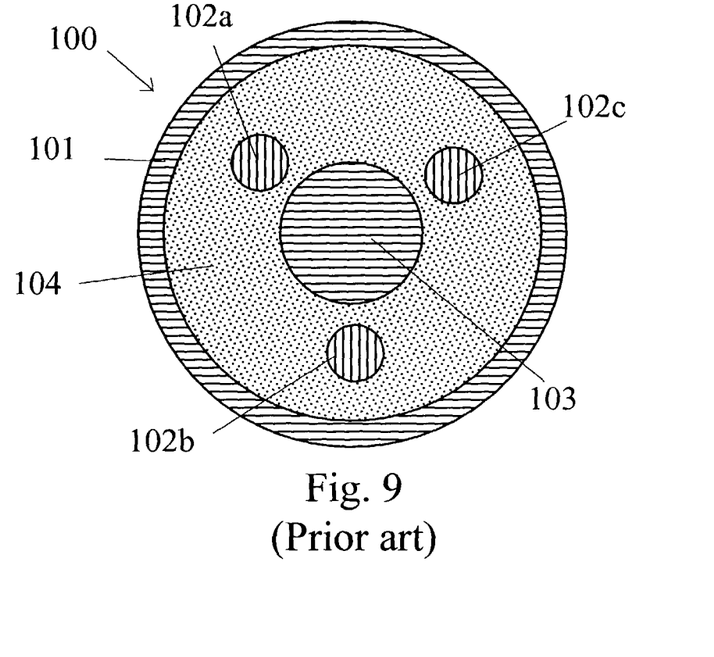
FIG. 9 is a longitudinal cross-sectional view through another prior art guide wire.

FIG. 9 illustrates a prior art guide wire 100 which comprises a hollow tube 101, in which three electrical leads 102a, 102b and 102c have been positioned around a central core 103. In practice, the leads were not displaced exactly 120 degrees apart and instead were just "spread out" around the core wire. The remaining space between the central core 103 and the inner lumen wall of the hollow tube 101, which is not occupied by the electrical leads 102a-c, has been filled with an insulating material 104. In particular, as is mentioned above, it should be noted that with this configuration the guide wire assembly 100 is not rotationally symmetric, which leads to different bending properties in different bending directions. In this context it should, however, also be recognized that the importance of rotational symmetry decreases radially towards the centre of a guide wire, i.e. it is generally more important that the outer portions of the guide wire are rotationally symmetric than those portions close to the centre of the guide wire. This last statement is illustrated in conjunction with FIG. 10 below.

Figure 10:
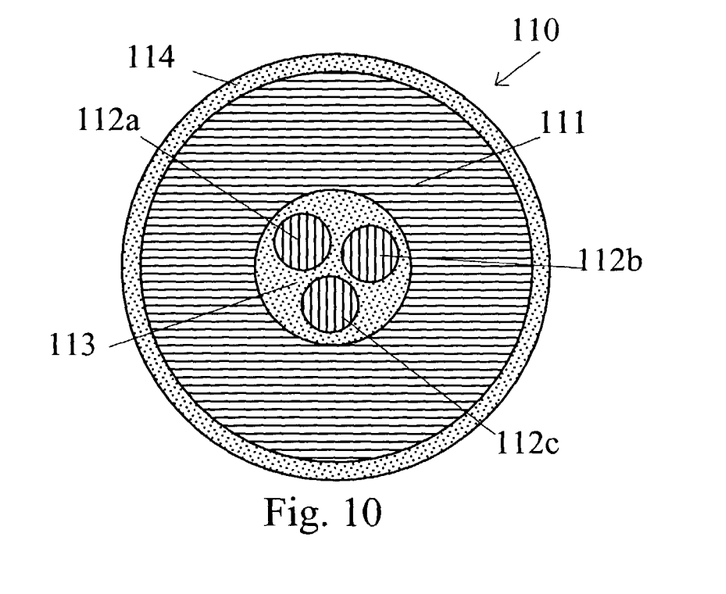
FIG. 10 illustrates a further embodiment of a guide wire assembly according to the invention.

FIG. 10 illustrates an alternative arrangement of three electrical leads 112a, 112b and 112c within a hollow tube 111 of a guide wire 110. In this arrangement, which also constitutes a first embodiment of the present invention, the three leads 112a-c are positioned within the hollow tube 111 and are surrounded by an insulating material 113. The hollow tube 111, which has a comparatively thick wall, can be made of an electrically conducting material with high strength, such as steel. An outer insulating layer 114 has been provided around the thick-walled tube 111. A comparison between the guide wire 100 of FIG. 9 and the guide wire 110 of FIG. 10 reveals that the latter exhibits at least two important advantages in comparison with the former. These two advantages are: 1) the guide wire 110 is more bending-resistant because the tube 111 contains more bending-resistant material, and 2) the bending properties of the guide wire 110 are essentially uniform in all directions. The last advantage implies that from a practical point of view, i.e. for the purposes of the present invention, the guide wire 110 according to FIG. 10 can be considered as being a rotationally symmetric guide wire 110.

Figure 11:
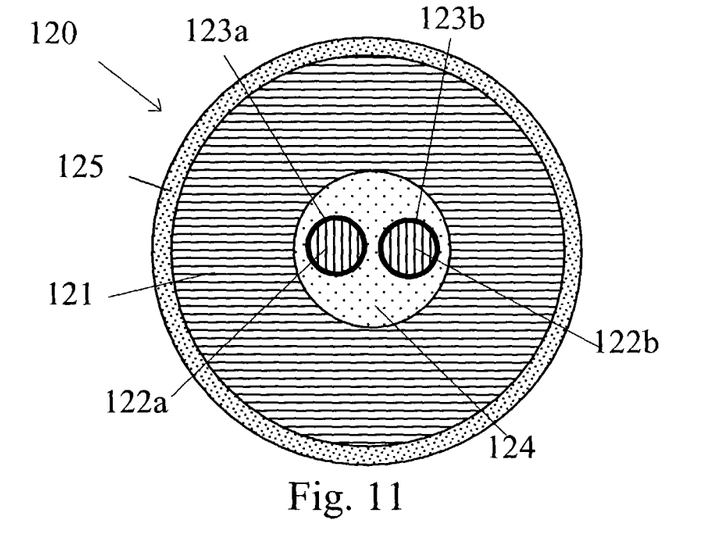
FIG. 11 illustrates a further embodiment of a guide wire assembly according to the invention.

In FIG. 11 a second embodiment of the present invention is illustrated. Here, only two leads 122a and 122b are positioned within a hollow tube 121 of a guide wire 120. The hollow tube 121, which has a thick wall, can be made of an electrically conducting material, such as steel, and according to the reasoning presented above also this arrangement is, for the purposes of the present invention, to be regarded as rotationally symmetric. In the embodiment shown in FIG. 11, each of the two leads 122a-b has been provided with a separate layer 123a and 123b, respectively, of an insulating material. The leads 122a and 122b can therefore be considered as insulated electrical leads 122a and 122b. Consequently, for insulating purposes no material has to be provided within the lumen of the hollow tube 121, which for the manufacture of the guide wire 120 can be advantageous. As an alternative, the space within the lumen of the hollow tube 121 that is not occupied by the leads 122a, 122b can, of course, be filled with an insulating material, and the reference number 124, which in FIG. 11 points at this position, can therefore refer to any non-conducting material, including air, or even to vacuum. If no material 124 is provided within the hollow tube 121, the sum of the diameters of the leads 122a, 122b can be made equal to the diameter of the lumen of the tube 121, to thereby prevent the leads 122a, 122b from moving within the lumen of the hollow tube 121. An outer insulating layer 125 covers the thick-walled tube 121.

Figure 12:
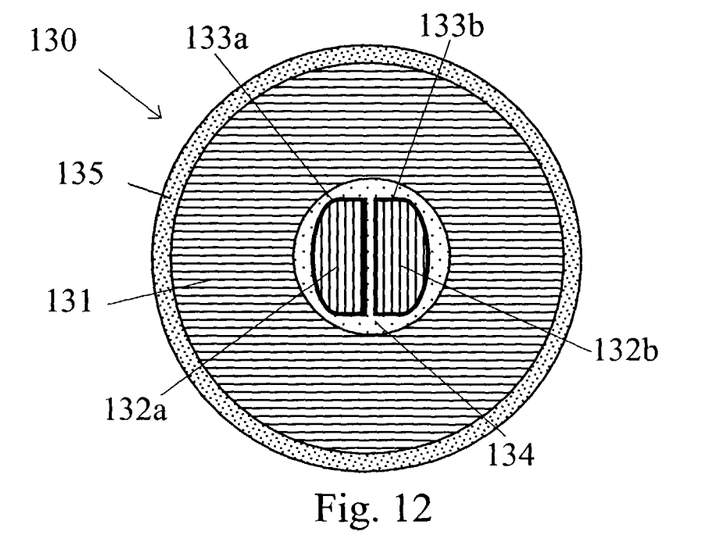
FIG. 12 illustrates a further embodiment of a guide wire assembly according to the invention.

According to the present invention, the electrically conducting leads can have different shapes, and in FIG. 12 a third embodiment of a guide wire 130 is shown. The guide wire comprises a hollow tube 131, which has a thick wall and is made of a conducting material and inside which two electrically conducting leads 132a and 132b are positioned. In this embodiment of the present invention, the leads 132a, 132b have semi-circular or D-shaped cross-sections, with the straight portions of the respective D-shape facing each other. With this configuration, the available space within the hollow tube 131 is efficiently utilized. Like the embodiment shown in FIG. 11, the electrically conducting leads 132a-b have each been provided with a separate layer 133a, 133b of an insulating material. The rest of the available space within the hollow tube 131, which is indicated by reference number 134, can in this case be filled with any non-conducting material, including air, or the space can be completely empty, i.e. vacuum. If the electrically conducting leads 132a-b are not provided with these separate layers 133a-b of insulating material, the rest of the available space within the lumen of the tube 131 is filled with an insulating material 134. An outer insulating layer 135 covers the thick-walled tube 131.

Figure 13:
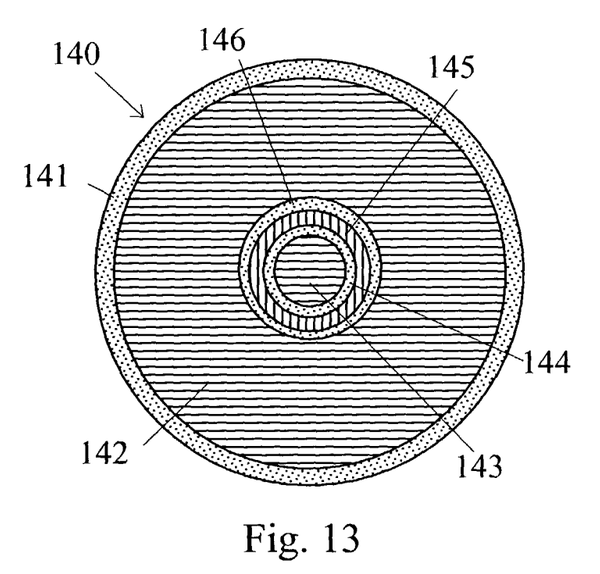
FIG. 13 illustrates a further embodiment of a guide wire assembly according to the invention.

A fourth embodiment of the present invention is shown in FIG. 13, where a guide wire 140 comprises an outer insulating layer 141, which covers a hollow tube 142. The hollow tube 142 has a thick wall and can be made of an electrically conducting material, such as steel. Within the lumen of the hollow tube 142, a central core 143 is provided. The central core 143 is made of an electrically conductive material and is surrounded by an insulating layer 144, which, in turn is surrounded by an inner tube 145. The inner tube 145 is made of an electrically conductive material and is surrounded by an insulating layer 146. With this arrangement, two electrically conductive members, the central core 143 and the inner tube 145, have been provided in a coaxial arrangement, which is completely rotationally symmetric.

Although the present invention has been described with reference to specific embodiments, also shown in the appended drawings, it will be apparent for those skilled in the art that many variations and modifications can be done within the scope of the invention as described in the specification and defined with reference to the following claims.

What is claimed is:

1. A sensor and guide wire assembly, comprising:
   a guide wire, including:
      a thick-walled hollow tube defining a lumen, the hollow tube being made of conductive material; and
      at least two electrical leads within the lumen;
   an electrical sensor attached proximate a distal end of the guide wire; and
   a connector attached to a proximal end of the guide wire, the connector including at least two conductors,
   wherein the thick-walled hollow tube, when evaluated in a plane normal to a longitudinal direction of the thick-walled hollow tube, has a cross-section that is rotationally symmetric and is uniform, and wherein a thickness of the hollow tube is at least 50% of a diameter of the lumen.

2. A sensor and guide wire assembly as set forth in claim 1, wherein the guide wire comprises at least three electrical leads within the lumen.

3. A sensor and guide wire assembly as set forth in claim 1, wherein the guide wire comprises at least three electrical leads within the lumen arranged approximately at vertices of an equilateral polygon whose center point corresponds to a center point of a cross-section of the guide wire.

4. A sensor and guide wire assembly as set forth in claim 1, wherein the guide wire comprises three electrical leads within the lumen arranged approximately at vertices of an equilateral triangle whose center point corresponds to a center point of a cross-section of the guide wire.

5. A sensor and guide wire assembly as set forth in claim 1, further comprising insulating material within the lumen.

6. A sensor and guide wire assembly as set forth in claim 1, further comprising insulating material on the outside of the hollow tube.

7. A sensor and guide wire assembly as set forth in claim 1, wherein the thickness of the hollow tube is at least 100% of the diameter of the lumen.

8. A sensor and guide wire assembly as set forth in claim 1, wherein the thickness of the hollow tube is at least 150% of the diameter of the lumen.

9. A sensor and guide wire assembly as set forth in claim 1, wherein the at least two electrical leads are each insulated.

10. A sensor and guide wire assembly as set forth in claim 1, wherein the at least two electrical leads are circular in cross-section.

11. A sensor and guide wire assembly as set forth in claim 1, wherein the at least two electrical leads are D-shaped in cross-section.

12. A sensor and guide wire assembly as set forth in claim 1, wherein the lumen is filled with a gas.

13. A sensor and guide wire assembly as set forth in claim 1, wherein one of the at least two electrical leads is surrounded by another of the at least two electrical leads.

14. A sensor and guide wire assembly as set forth in claim 13, wherein one of the at least two electrical leads is circular in cross-section and another of the at least two electrical leads is annular in cross-section.

15. A sensor and guide wire assembly as set forth in claim 13, further comprising insulating material separating the at least two electrical leads from one another.

16. A sensor and guide wire assembly as set forth in claim 1, wherein the at least two electrical leads within the lumen are not concentric with one another and are not concentric with the lumen.

17. A sensor and guide wire assembly as set forth in claim 16, wherein the guide wire comprises at least three electrical leads within the lumen arranged approximately at vertices of an equilateral polygon whose center point corresponds to a center point of a cross-section of the guide wire.

18. A sensor and guide wire assembly as set forth in claim 1, further comprising insulating material provided between the tube and at least one of the at least two electrical leads within the lumen.

19. A sensor and guide wire assembly as set forth in claim 1, wherein the assembly is adapted such that energizing current can be supplied through at least one of the electrical leads for energizing the electrical sensor and the at least one electrical lead can also be used for transmissions of signals from the electrical sensor by modulating the energizing current.

20. A sensor and guide wire assembly as set forth in claim 1, wherein the guide wire is about 1.8 meters to about 3 meters in length.

21. A sensor and guide wire assembly as set forth in claim 1, wherein the electrical sensor is a sensor chip.

22. A sensor and guide wire assembly as set forth in claim 21, wherein the thick-walled hollow tube defining the lumen has a substantial recess formed in the tube in an area proximate the distal end of the guide wire, wherein the sensor chip lies in the recess.

23. A sensor and guide wire assembly as set forth in claim 1, wherein the thick-walled hollow tube defining the lumen substantially narrows in outer diameter in an area proximate to the distal end of the guide wire.

24. A sensor and guide wire assembly as set forth in claim 23, wherein the guide wire comprises at least three electrical leads within the lumen arranged approximately at vertices of an equilateral polygon whose center point corresponds to a center point of a cross-section of the guide wire.

25. A sensor and guide wire assembly as set forth in claim 1, wherein in an area proximate the distal end of the guide wire, the thick-walled hollow tube defining the lumen comprises a portion forming a mounting structure for the electrical sensor, and wherein the mounting structure comprises a recess exposing the electrical leads and forming a contact surface for the sensor.

26. A sensor and guide wire assembly as set forth in claim 1, wherein the tube and at least one of the electrical leads are in electrical communication with each other.

27. A sensor and guide wire assembly as set forth in claim 1, wherein the sensor is directly exposed to an exterior environment of the sensor and guide wire assembly.

28. A sensor and guide wire assembly as set forth in claim 1, wherein the sensor is a pressure sensor.

29. A sensor and guide wire assembly as set forth in claim 1, wherein the sensor is disposed in a slot in the sensor and guide wire assembly, and wherein sidewalls inside the slot extend above an upper surface of the sensor in a direction towards an exterior environment of the sensor and guide wire assembly.

30. A sensor and guide wire assembly as set forth in claim 1, wherein the sensor is disposed in a slot in the sensor and guide wire assembly, and wherein a coil covers at least a fraction of the slot with respect to an exterior environment of the sensor and guide wire assembly.

31. A sensor and guide wire assembly as set forth in claim 1, wherein the guide wire has an outer diameter, when evaluated in the plane, of about 0.35 mm.

32. A sensor and guide wire assembly as set forth in claim 1, wherein the guide wire has a length of about 1.8 m or longer.

33. A sensor and guide wire assembly as set forth in claim 1, wherein the lumen, when evaluated in the plane, is about concentric with an outer diameter of the thick-walled hollow tube.

34. A sensor and guide wire assembly as set forth in claim 1, wherein the thick-walled hollow tube is a core wire.

35. A sensor and guide wire assembly, comprising:
a guide wire, including:
a thick-walled hollow tube defining a lumen, the hollow tube being made of conductive material; and
at least two electrical leads within the lumen;
an electrical sensor attached proximate a distal end of the guide wire; and
a connector attached to a proximal end of the guide wire, the connector including at least two conductors,
wherein the tube is in electrical conductive relationship with the electrical sensor, and wherein a thickness of the hollow tube is at least 50% of a diameter of the lumen.

36. A sensor and guide wire assembly as set forth in claim 35, wherein the tube and at least one of the electrical leads are in electrical communication with each other.

37. A sensor and guide wire assembly as set forth in claim 35, wherein the thick-walled hollow tube is rotationally symmetric.

38. A sensor and guide wire assembly as set forth in claim 35, wherein the sensor is a sensor chip.

39. A sensor and guide wire assembly as set forth in claim 35, wherein the thick-walled hollow tube is a core wire.

* * * * *